United States Patent
Han

(10) Patent No.: US 8,156,944 B2
(45) Date of Patent: Apr. 17, 2012

(54) AEROSOL ELECTRONIC CIGARETTE

(75) Inventor: Li Han, Hong Kong (CN)

(73) Assignee: Ruyan Investments (Holdings) Limited, Hong Kong (HK)

( * ) Notice: Subject to any disclaimer, the term of this patent is extended or adjusted under 35 U.S.C. 154(b) by 395 days.

(21) Appl. No.: 12/226,818

(22) PCT Filed: May 15, 2007

(86) PCT No.: PCT/CN2007/001575
§ 371 (c)(1),
(2), (4) Date: Oct. 29, 2008

(87) PCT Pub. No.: WO2007/131449
PCT Pub. Date: Nov. 22, 2007

(65) Prior Publication Data
US 2009/0095311 A1    Apr. 16, 2009

(30) Foreign Application Priority Data

May 16, 2006 (CN) .................... 2006 2 0090805 U

(51) Int. Cl.
A24F 47/00 (2006.01)
A24F 1/32 (2006.01)
A61M 15/06 (2006.01)

(52) U.S. Cl. .... 131/273; 131/360; 131/194; 128/202.21
(58) Field of Classification Search .................. 131/194, 131/270–273, 360; 128/200.14, 202.21
See application file for complete search history.

(56) References Cited

U.S. PATENT DOCUMENTS

| | | |
|---|---|---|
| 4,228,925 A | 10/1980 | Mendelovich |
| 4,641,053 A | 2/1987 | Takeda |
| 4,848,374 A | 7/1989 | Chard |
| 4,945,929 A | 8/1990 | Egilmex |
| 4,945,931 A | 8/1990 | Gori |
| 5,042,470 A | 8/1991 | Kanesaka |
| 5,060,671 A | 10/1991 | Counts et al. |
| 5,080,114 A | 1/1992 | Rudolph et al. |
| 5,095,921 A | 3/1992 | Losee |
| 5,159,940 A | 11/1992 | Hayward et al. |
| 5,190,060 A | 3/1993 | Gerding |
| 5,249,586 A | 10/1993 | Morgan et al. |

(Continued)

FOREIGN PATENT DOCUMENTS

CA        2562581        10/2005

(Continued)

OTHER PUBLICATIONS

State Intellectual Property Office (China), International Search Report for PCT/CN07/001575, Aug. 16, 2007.
State Intellectual Property Office (China), English Translation of the Written Opinion for PCT/CN07/001575, Jul. 20, 2007.
State Intellectual Property Office (China), International Search Report for PCT/CN07/001576, Aug. 16, 2007.

(Continued)

Primary Examiner — Richard Crispino
Assistant Examiner — Dionne Walls Mayes
(74) Attorney, Agent, or Firm — Perkins Coie LLP

(57) ABSTRACT

An aerosol electronic cigarette includes a battery assembly, an atomizer assembly and a cigarette bottle assembly and also includes a shell (a) which is hollow and integrally formed. Said battery assembly connects with said atomizer assembly and both are located in said shell (a). Said cigarette bottle assembly is located in one end of the shell (a), which is detachable. Said cigarette bottle assembly fits with said atomizer assembly. Said shell (a) has through-air-inlets (a1).

41 Claims, 8 Drawing Sheets

U.S. PATENT DOCUMENTS

| | | | |
|---|---|---|---|
| 5,261,424 | A | 11/1993 | Sprinkel, Jr. |
| 5,285,798 | A | 2/1994 | Banerjee |
| 5,322,075 | A | 6/1994 | Deevi |
| 5,666,978 | A | 9/1997 | Counts |
| 5,743,251 | A | 4/1998 | Howell |
| 5,746,251 | A | 5/1998 | Bullard |
| 5,878,752 | A | 3/1999 | Adams et al. |
| 5,894,841 | A | 4/1999 | Voges |
| 6,040,560 | A | 3/2000 | Fleischhauer |
| 6,041,789 | A | 3/2000 | Bankert |
| 6,164,287 | A | 12/2000 | White |
| 6,178,969 | B1 | 1/2001 | St. Charles |
| 6,196,218 | B1 * | 3/2001 | Voges .................. 128/200.14 |
| 6,357,671 | B1 | 3/2002 | Cewers |
| 6,443,146 | B1 | 9/2002 | Voges |
| 6,532,965 | B1 | 3/2003 | Abhulimen |
| 6,772,756 | B2 | 8/2004 | Shayan |
| 6,803,545 | B2 | 10/2004 | Blake |
| 6,854,461 | B2 | 2/2005 | Nichols |
| 7,131,599 | B2 | 11/2006 | Katase |
| 7,845,359 | B2 | 12/2010 | Montaser |
| 2003/0108342 | A1 | 6/2003 | Sherwood et al. |
| 2004/0261802 | A1 | 12/2004 | Griffin et al. |
| 2005/0016550 | A1 | 1/2005 | Katase |
| 2005/0236006 | A1 | 10/2005 | Cowan |
| 2006/0196518 | A1 * | 9/2006 | Hon .................. 131/360 |
| 2007/0267031 | A1 * | 11/2007 | Hon .................. 131/273 |
| 2008/0276947 | A1 | 11/2008 | Martzel |
| 2009/0151717 | A1 | 6/2009 | Bowen |
| 2009/0230117 | A1 | 9/2009 | Fernando |
| 2009/0260642 | A1 | 10/2009 | Monsees |
| 2009/0272379 | A1 | 11/2009 | Thorens |
| 2010/0031968 | A1 | 2/2010 | Sheikh |
| 2010/0126505 | A1 | 5/2010 | Rinker |
| 2010/0181387 | A1 | 7/2010 | Zaffaroni |
| 2010/0200008 | A1 | 8/2010 | Taieb |
| 2010/0242974 | A1 | 9/2010 | Pan |
| 2010/0307518 | A1 | 12/2010 | Wang |
| 2011/0005535 | A1 | 1/2011 | Xiu |
| 2011/0036346 | A1 | 2/2011 | Cohen |

FOREIGN PATENT DOCUMENTS

| | | | |
|---|---|---|---|
| CN | 2047485 | U | 11/1989 |
| CN | 2047485 | U | 11/1989 |
| CN | 1135860 | | 11/1996 |
| CN | 1106812 | C | 10/1998 |
| CN | 2293957 | Y | 10/1998 |
| CN | 97216131 | | 10/1998 |
| CN | 1252961 | | 5/2000 |
| CN | 1530041 | A | 9/2004 |
| CN | 2643681 | | 9/2004 |
| CN | 2648836 | | 10/2004 |
| CN | 1541577 | A | 11/2004 |
| CN | 1575673 | A | 2/2005 |
| CN | 2719043 | * | 8/2005 |
| CN | 2719043 | Y | 8/2005 |
| CN | 2777995 | Y | 5/2006 |
| CN | 101084801 | | 12/2007 |
| CN | 1196660 | | 3/2010 |
| DE | 10051792 | | 5/2002 |
| EP | 0295122 | | 12/1988 |
| EP | 0342538 | | 11/1989 |
| EP | 0545186 | | 6/1993 |
| EP | 0824927 | A | 2/1998 |
| EP | 0845220 | A1 | 6/1998 |
| EP | 0893071 | A1 | 1/1999 |
| EP | 0970627 | A1 | 1/2000 |
| EP | 1618803 | A1 | 1/2006 |
| EP | 1736065 | A1 | 12/2006 |
| GB | 1528391 | A | 10/1978 |
| JP | 64000498 | | 1/1989 |
| JP | 06114105 | | 4/1994 |
| JP | 07506999 | | 8/1995 |
| JP | 09075058 | | 3/1997 |
| UA | 47514 | | 12/1997 |
| WO | WO9748293 | | 12/1997 |
| WO | WO00049901 | | 8/2000 |
| WO | WO0050111 | | 8/2000 |
| WO | WO03034847 | | 1/2003 |
| WO | WO03022364 | | 3/2003 |
| WO | WO03055486 | | 7/2003 |
| WO | WO03101454 | | 12/2003 |
| WO | WO2004001407 | A1 | 12/2003 |
| WO | 2004080216 | | 9/2004 |
| WO | WO2004080216 | | 9/2004 |
| WO | 2004095955 | | 11/2004 |
| WO | WO 2004/095955 | * | 11/2004 |
| WO | 2005099494 | | 10/2005 |
| WO | 2007131449 | | 11/2005 |
| WO | WO2006082571 | | 8/2006 |
| WO | WO2007078273 | | 7/2007 |
| WO | 2007131450 | | 11/2007 |
| WO | 2008055423 | | 5/2008 |
| WO | WO2008077271 | | 7/2008 |
| WO | WO2008130813 | | 10/2008 |
| WO | WO2009118085 | | 10/2009 |
| WO | WO2009135729 | | 11/2009 |
| WO | WO2010052323 | | 5/2010 |
| WO | WO2010145805 | | 12/2010 |
| WO | WO2011010334 | | 1/2011 |
| WO | WO2011022431 | | 2/2011 |

OTHER PUBLICATIONS

State Intellectual Property Office (China), English Translation of the Written Opinion for PCT/CN07/001576, Aug. 3, 2007.

European Patent Office, extended European Search Report for EP 07721148, Dec. 6, 2010.

European Patent Office, extended European Search Report for EP 11001479, Jul. 4, 2011.

Introduction to Selecting and Using Electronic Components, ISBN7-111-13752-3.

Manual for Electric Engineers, 2nd Edition, Mar. 2000.

Manual for Mechanical Designers, 4th Edition, Jan. 2002.

Materials Manual—Nonmetal, Jul. 1985.

Australian Patent Office, Examination Report for SG 200505930-8, May 4, 2006.

Australian Patent Office; Exam Report for AU2004234199, Aug. 14, 2009.

Australian Patent Office; Search and Examination Report for SG200604498-6, Apr. 16, 2008.

Australian Patent Office; Singapore Examination Report for Singapore Patent Application No. 0604498-6 SG 200505930-8, May 13, 2008.

Chinese Patent Office, International Search Report for International Application No. PCT/CN2004000182, Jun. 10, 2004.

Chinese Patent Office, International Search Report for International Application No. PCT/CN2005/000337, Jul. 14, 2005.

European Patent Office, Supplementary European Search Report for EP05729107, Jul. 31, 2007.

European Patent Office, Supplementary European Search Report for EP04718242, Jul. 27, 2007.

European Patent Office, Supplementary Partial European Search Report for EP04718242, May 22, 2007.

European Patent Office, Supplementary Partial European Search Report for EP05729107, May 22, 2007.

Japanese Patent Office; Office Action for JP2006504199, Oct. 30, 2009 (with English translation).

Korean Patent Office; Notice of Preliminary Rejection for KR1020057009767, Jul. 27, 2009.

Macau Patent Office; Official Communication for MOI121, Apr. 17, 2009.

Malaysia Intellectual Property Office; Examiners Report for Malaysian Application No. PI 20041407, Sep. 28, 2007.

Taiwan Intellectual Property Office; Official Letter for TW093111573, Apr. 24, 2009.

Ukrainian Patent Office; Examination Report for UA200511258, Feb. 4, 2009.

* cited by examiner

AEROSOL ELECTRONIC CIGARETTE

TECHNICAL FIELD

The present invention relates to an electronic cigarette, in particular, an aerosol electronic cigarette that doesn't contain tar but nicotine.

BACKGROUND ART

Today when "smoking is harmful to your health" has become a common sense, there are one billion people smoking cigarettes, and this figure is still rising. On Mar. 1, 2003, the World Health Organization (WHO) issued the first international smoking ban—Framework Convention on Tobacco Control. According to WHO's data, smoking causes 4,900,000 deaths each year. Smoking causes serious respiratory system diseases and cancers, though it is a hard job to persuade the smokers to completely quit smoking.

Nicotine is the effective ingredient of cigarette, which produces a lot of tar mist as the cigarette burns. The tar mist accesses the pulmonary alveolus and is quickly absorbed into the blood. Nicotine thus acts on the receptor of the central nervous system, bringing the euphoria like stimulant drugs to the smokers, who feel light in the head and on wings as well.

Nicotine is a micromolecular alkaloid, which is basically harmless to human bodies with a small dosage. Plus, its half life period is extremely short in blood. Tar is the major harmful substance in tobacco. Tobacco tar comprises of several thousands of ingredients, dozens of which are carcinogenic substances. It has now been proved that second hand smoking is even more harmful to those who don't smoke.

To seek the cigarette substitutes that don't contain harmful tar but nicotine, many inventors have used the relatively pure nicotine to create such products as "Cigarette Patch", "Nicotine Gargle", "Aerosol Packed in the High Pressure Tank with Propellant", "Nicotine Chewing Gum", and "Nicotine Beverage". These products are not as harmful as tar, but are absorbed very slowly. As a result, its peak concentration can't be effectively established in blood, and the smokers can't be satisfied to the full. In addition, the smokers are deprived of the "smoking" habit. Therefore, the substituting products are not real cigarette substitutes or products helping to quit smoking.

The electronic cigarettes currently available on the market may resolve the above-mentioned issue, though they are complicated in structure. Their cigarette bodies can be roughly divided into three sections, which have to be connected through via plugging or thread coupling before use. Also, their batteries have to be changed frequently, making it inconvenient for the users. What's worse, the electronic cigarettes don't provide the ideal aerosol effects, and their atomizing efficiency is not high.

CONTENTS OF INVENTION

To overcome the above-mentioned disadvantages, this invention has been designed to provide an aerosol electronic cigarette that substitutes for cigarettes and helps the smokers to quit smoking.

The purpose of this invention is fulfilled with the following technical solution: an aerosol electronic cigarette includes a battery assembly, an atomizer assembly and a cigarette bottle assembly, and also includes a shell, which is hollow and integrally formed. The said battery assembly connects with the said atomizer assembly and both are located in the said shell. The said cigarette bottle assembly is located in one end of the shell, which is detachable. The said cigarette bottle assembly fits with the said atomizer assembly. The said shell has through-air-inlets.

The additional features of this invention are as follows: the said battery assembly includes the battery, and the operating indicator, electronic circuit board, and airflow sensor, which are connected with the said battery; the signal output of the said airflow sensor is connected with the said electronic circuit board.

It also includes a check valve. The said battery is a rechargeable battery, which has a flexibly connected charging plug. The blades of the said plug come out of the other end of the said shell.

Between the said charging plug and rechargeable battery is a spring, which lies against the body of the said rechargeable battery on one end, and its free end lies against the said charging plug.

The said battery is a rechargeable battery, which has a charging slot on it. The said operating indicator is a LED.

The said airflow sensor may be alternatively a semiconductor force-sensitive chip capacitance sensor or an inductance sensor.

The said electronic circuit board includes an electronic switch circuit.

The said airflow sensor has a silica gel corrugated membrane, which connects with magnetic steel with a reed relay on one of its ends. Both ends of the said reed relay correspond to the relay electrodes.

The said airflow sensor has a silica gel corrugated membrane, which connects with magnetic steel with a Hall element or a magneto-diode or a magneto-triode on one of its ends.

The said atomizer assembly is an atomizer, which includes a porous component and a heating body.

The said atomizer also includes an electric heating rod. The body of the said porous component has a run-through atomizing chamber. The diameter of the said electric heating rod is less than the diameter of the said atomizing chamber. The said electric heating rod enters into the said atomizing chamber, and there is a clearance between the said electric heating rod and interior wall of the atomizing chamber. The said clearance forms a negative pressure cavity. One end of the said porous component fits with the said cigarette bottle assembly.

The said electric heating rod includes a cylinder. The said heating body is heating wire, which is wound on the wall of the said cylinder. The said porous component has a protuberance on one end, and the said protuberance fits with the said cigarette bottle assembly. The said protuberance is a half sphere, on the side of which there is a run-through hole connecting to the said atomizing chamber.

The said electric heating rod includes a cylinder. The said heating body is made of electrically conductive ceramic PTC material. The said heating body is set on the wall of the said cylinder. On the wall of both ends of the said cylinder, there are mandrils respectively. The said porous component has a protuberance on one end, and the said protuberance fits with the said cigarette bottle assembly. The said protuberance is a half sphere, on the side of which there is a run-through hole connecting to the said atomizing chamber.

The said heating body is heating wire. The said atomizer assembly includes a frame. The said porous component is set on the said frame. The said porous component is wound with heating wire. The said frame has a run-through hole on it. The said porous component is wound with heating wire in the part that is on the side in the axial direction of the said run-through hole. One end of the said porous component fits with the said cigarette bottle assembly.

The said porous component is made of foamed nickel, stainless steel fiber felt, macromolecular polymer foam or foamed ceramics.

The said heating wire is made of platinum wire, nickel-chromium alloy wire or iron-chromium alloy wire containing rare earth, or is flaked.

A restriction component, which is detachable, is set on one end of the said porous component. There is a restriction hole on the body of the said restriction component. The said restriction hole corresponds to the said atomizing chamber. The pore diameter of the said restriction hole is less than the inner diameter of the atomizing chamber.

The said cigarette bottle assembly includes a hollow cigarette holder shell, and a perforated component for liquid storage inside the said cigarette holder shell. One end of the said cigarette holder shell plugs into the said shell, and the outer peripheral surface of the said cigarette holder shell has an inward ventilating groove. On one end surface of the said cigarette holder shell, there is an air channel extending inward.

The said air channel is located in the center on one end surface of the said cigarette holder shell.

One end of the said porous component lies against one end surface of the said perforated component for liquid storage, and contacts the said perforated component for liquid storage.

The said perforated component for liquid storage is made of such materials as PLA fiber, terylene fiber or nylon fiber.

The said perforated component for liquid storage is plastic foam molding or column of multi-layer plates made through plastic injection with polyvinyl chloride, polypropylene and polycarbonate.

The said electronic cigarette is held in a charging device.

The said charging device includes a case, which contains an auxiliary charging storage battery inside it, and holds the electronic cigarette and the charger for the rechargeable battery embedded in the electronic cigarette, as well as the power supply circuit. The power inputs of the said auxiliary charging storage battery and charger are connected with the power supply circuit respectively.

The said case has a spare liquid supply bottle in it.

The power output of the said auxiliary charging storage battery is connected with the power input of the said charger.

The power output of the said charger is a charging slot, which fits with the charging plug of the rechargeable battery inside the said electronic cigarette, or a charging plug, which fits with the charging slot of the rechargeable battery.

The said charger is a constant voltage & current charger.

On the body of the said shell, there is a pair of slide ways corresponding to the position of the said electronic cigarette, and on the slide ways, there is a slide cover.

This invention will bring the following benefits: (1) For this invention, the perforated component for liquid storage of the cigarette bottle assembly stores the nicotine liquid only, which doesn't contain cigarette tar, considerably reducing the carcinogenic risks of smoking. At the same time, the smokers can still enjoy the feel and excitement of smoking, and there is no fire hazard since there is no need for igniting. (2) For this invention, the battery assembly and atomizer assembly are directly installed inside the shell, and then connected with the cigarette bottle assembly. That is, there is just one connection between two parts, resulting in a very simple structure. For use or change, you just need to plug the cigarette holder into the shell, providing great convenience. When the nicotine liquid in the cigarette bottle assembly is used up or the cigarette bottle assembly is damaged and needs to be changed, the operation will be extremely easy. (3) For this invention, the rechargeable battery inside the battery assembly has a charging plug, whose blades come out of the shell. When the rechargeable battery inside the electronic cigarette runs out of power, it may be directly plugged into the charger for charging, with no need to remove the rechargeable battery, resulting in very easy use. (4) For this invention, the charging device includes the charger and the auxiliary charging storage battery. The electronic cigarette is put inside the charger when not in use, and then the charging device may be electrified to charge the electronic cigarette and the auxiliary charging storage battery as well. In the event that power supply is not available for the charging device, the auxiliary charging storage battery may be used to charge the electronic cigarette. Therefore, the electronic cigarette can be charged anywhere you go, and it is very suitable for use when you are on a business or tourist trip. Further, the charging device includes a spare liquid supply bottle, which contains nicotine liquid for spare use when you are on a business or tourist trip. (5) For this invention, on one end of the shell of the cigarette bottle assembly, there is an air channel extending inward. The electronic cigarette works to produce mist, which flows to the shell, generating some fine drips; the fine drips are condensed into bigger drips, which fall along the exterior wall of the air channel into the cavity of the shell of the cigarette bottle assembly, so that they are not inhaled by the smoker out of the air channel. (6) In addition, with a little bit modification to the liquid storage, the unit and its connecting structure of this invention may also be loaded with drugs for delivery to the lung.

SPECIFIC MODE FOR CARRYING OUT THE INVENTION

Figure 1:
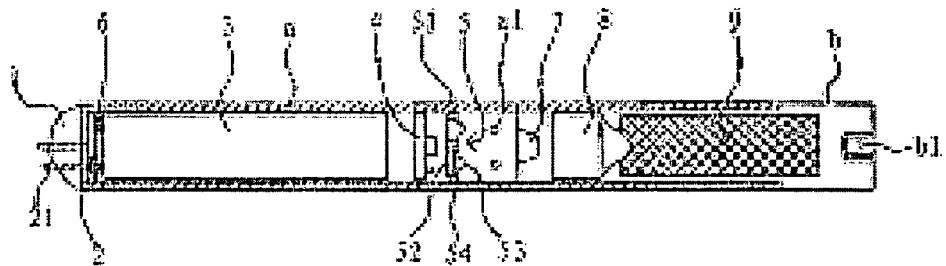
FIG. 1 is the side section view of the electronic cigarette of this invention.

This invention is further described as follows on the basis of the drawings.

As shown in FIG. 1-10, this utility model provides an aerosol electronic cigarette, which includes a battery assembly, an atomizer assembly and a cigarette bottle assembly, and also includes a shell (a), which is hollow and integrally formed. The battery assembly connects with the atomizer assembly and both are located in the shell. The cigarette bottle assembly is located in one end of the shell, which is detachable. The cigarette bottle assembly fits with the atomizer assembly. The shell has through-air-inlets (a1).

In this specific embodiment, the battery assembly includes the battery, and the operating indicator (1), electronic circuit board (4), and airflow sensor (5), which are connected with the battery. It also includes a check valve (7). The signal output of the airflow sensor (5) is connected with the said electronic circuit board (4). The battery is a rechargeable battery (3), which may be either a rechargeable polymer lithium ion battery or a rechargeable lithium ion battery. The airflow sensor (5) may be alternatively a semiconductor force-sensitive chip capacitance sensor or an inductance sensor. The rechargeable battery (3) has a flexibly connected charging plug (2). The blades (21) of the charging plug (2) come out of the other end of the shell (a). Between the charging plug (2) and rechargeable battery (3) is a spring (6), which lies against the body of the rechargeable battery (3) on one end, while its free end lies against the charging plug (2), forming a flexible structure, which buffers the charging plug (2) when plugged for charging, thus protecting the rechargeable battery (3) against any damage. Of course, the rechargeable battery (3) in this embodiment has a charging slot on it, which replaces the structure of charging plug (2) to perform the charging function and protect the rechargeable battery (3) against any damage. The operating indicator (1) is a LED. In this embodiment, there are two LEDs. The electronic circuit board (4) includes an electronic switch circuit, which controls the electric circuit according to the input signals, so that the rechargeable battery (3) electrifies the electric heating rod (82) inside the atomizer (8) and the LEDs as well.

Figure 2:
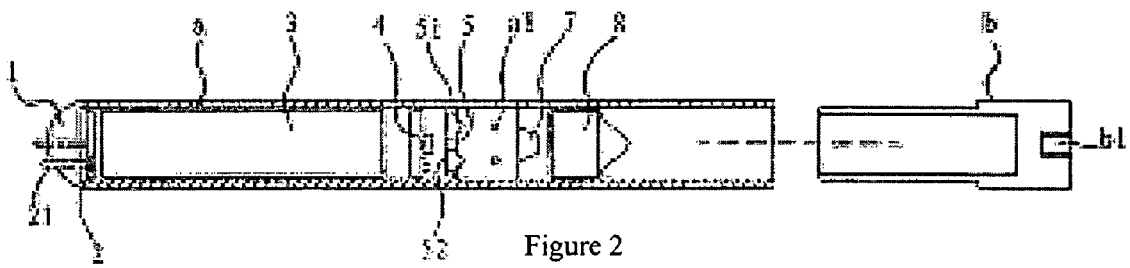
FIG. 2 is the section view of the shell (a) separated from the cigarette bottle assembly of the electronic cigarette of this invention, illustrating the structure of the cigarette bottle assembly that is detachably plug in the shell (a).
Figure 3:
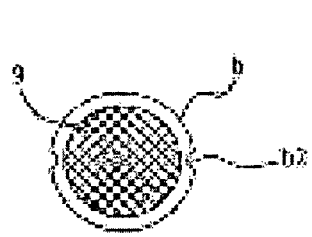
FIG. 3 is the diagram of the axial structure of the cigarette bottle assembly of this invention, illustrating the ventilating groove on the peripheral surface of the cigarette holder shell.
Figure 4:
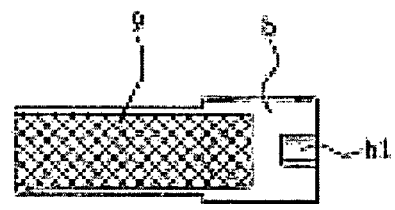
FIG. 4 is the side section view of the cigarette bottle assembly of this invention, illustrating the structure of the air channel.

As shown in FIGS. 1 and 2, the airflow sensor (5) has a silica gel corrugated membrane (53), which connects with magnetic steel (54) with a reed relay (52) on one of its ends. Both ends of the said reed relay (52) correspond to the relay electrodes (51) respectively.

Figure 5:
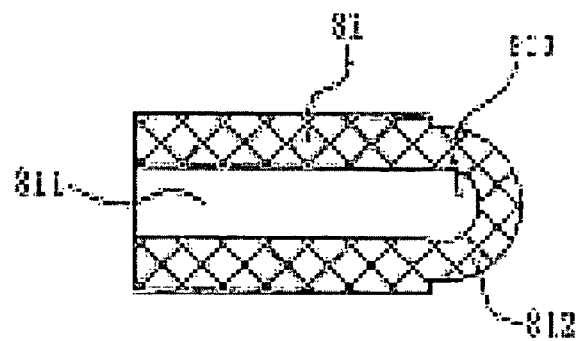
FIG. 5 is the side section view of the porous component of the atomizer of this invention, illustrating the atomizing chamber, a protruding half sphere structure.
Figure 6:
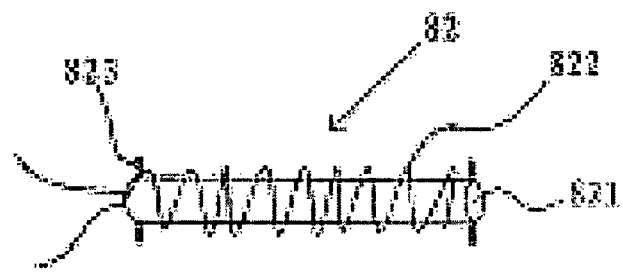
FIG. 6 is the diagram of the structure of the electric heating rod of the atomizer of this invention.
Figure 7:
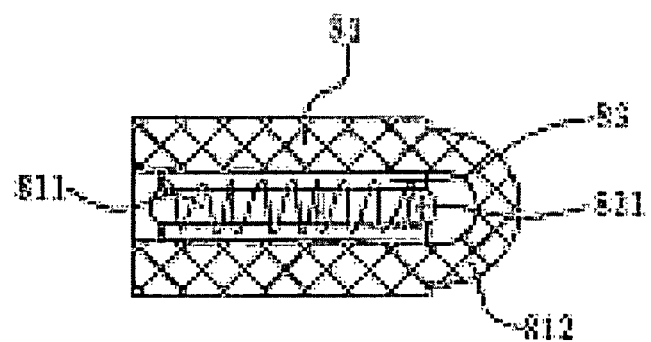
FIG. 7 is the side section of the atomizer of this invention, illustrating the locations of and connection relation between the electric heating rod and porous component.
Figure 8:
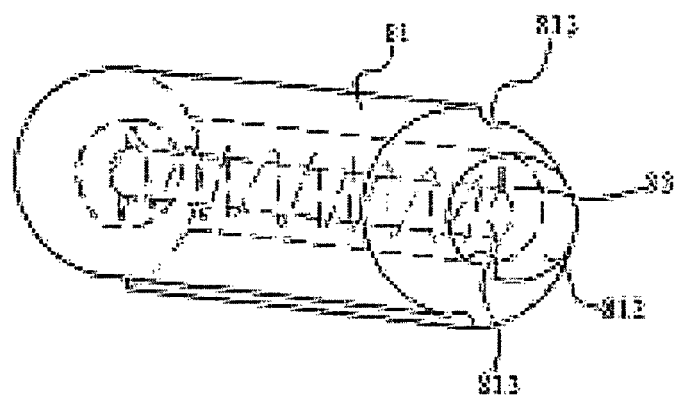
FIG. 8 is the diagram of the cubic structure of the atomizer of this invention, illustrating the locations of and connection relation between the electric heating rod and porous component.
Figure 9:
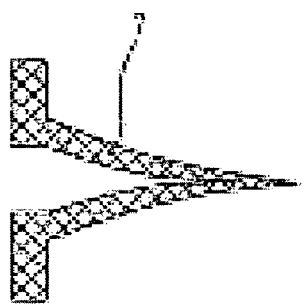
FIG. 9 is the section view of the check valve of this invention.
Figure 10:
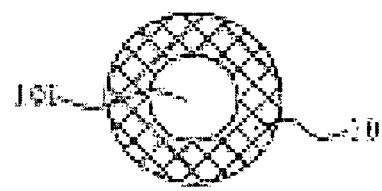
FIG. 10 is the front section view of the restriction component in the second preferred embodiment of this invention, illustrating the structure of the restriction component.
Figure 11:
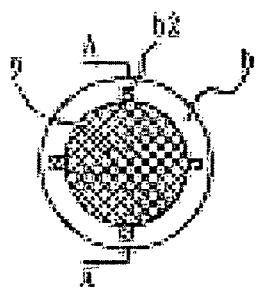
FIG. 11 is the diagram of the axial structure of the cigarette bottle assembly in the third preferred embodiment of this invention.
Figure 12:
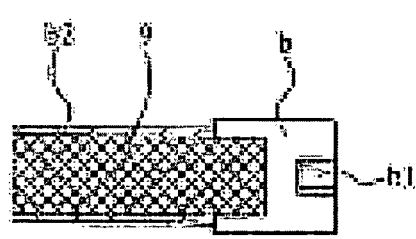
FIG. 12 is the A-A section view of FIG. 11.
Figure 13:
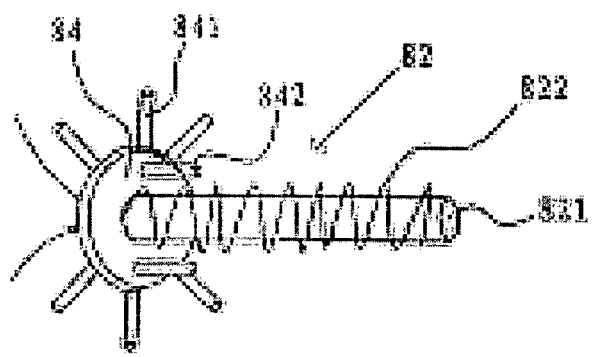
FIG. 13 is the diagram of the structure of the electric heating rod of the atomizer in the fourth preferred embodiment of this invention.
Figure 14:
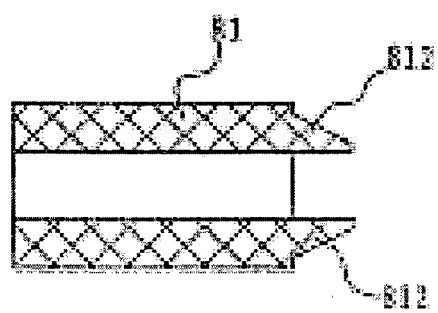
FIG. 14 is the section view of the porous component of the atomizer in the fourth preferred embodiment of this invention.
Figure 15:
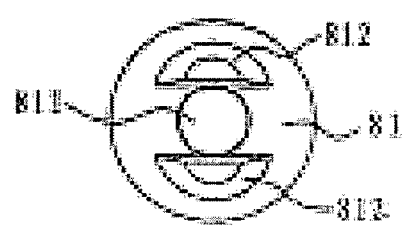
FIG. 15 is the diagram of the axial structure of FIG. 14.
Figure 16:
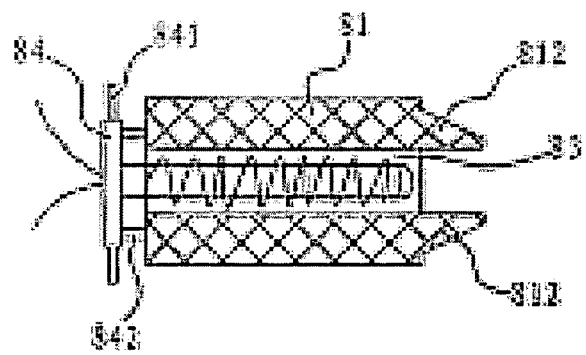
FIG. 16 is the side section view of the atomizer in the fourth preferred embodiment of this invention, illustrating the locations of and connection relation between the electric heating rod and porous component.

As shown in FIG. 5-8, the atomizer assembly is an atomizer (8), which includes a porous component (81) and a heating rod (82). The body of the porous component (82) has a run-through atomizing chamber (811). The diameter of the electric heating rod (82) is less than the diameter of the atomizing chamber (811). The electric heating rod (82) enters into the atomizing chamber (811), and there is a clearance between the electric heating rod (82) and interior wall of the atomizing chamber (811), which forms a negative pressure cavity (83). One end of the said porous component (81) fits with the said cigarette bottle assembly. As FIGS. 5, 7 and 8 show, the porous component (81) has a protuberance (812) on the other end, and the protuberance (812) fits with the cigarette bottle assembly. The protuberance (812) is a protruding half sphere, on the side of which there is a run-through hole (813) connecting to the atomizing chamber (811). Of course, the protuberance (812) may also be a taper, rectangle or any other shape. The porous component (81) is made of foamed nickel, stainless steel fiber felt, macromolecular polymer foam or foamed ceramics, providing the remarkable capabilities in liquid absorption and diffusion, and the ability to absorb the liquid stored in the cigarette bottle assembly.

As shown in FIG. 6, the electric heating rod (82) includes a cylinder (821). The heating wire (822) is wound on the wall of the cylinder (821). On the wall of both ends of the cylinder (821), there are mandrils (823) respectively, which lie against the interior wall of the atomizing chamber (811) of the porous component (81). There is a negative pressure cavity (83) between the electric heating rod and interior wall of the atomizing chamber.

The heating wire is made of platinum wire, nickel-chromium alloy wire or iron-chromium alloy wire containing rare earth, or is flaked. The electric heating rod (82) may alternatively have on its peripheral wall the heating layer made of electrically conductive ceramic PTC material, to replace the heating wire.

Of this embodiment, the battery assembly and atomizer assembly are mutually connected and then installed inside the integrally formed shell (a) to form a one-piece part. The rechargeable battery (3) may be charged without frequent change of battery. The user just needs to plug the cigarette bottle assembly into the open end of the shell (a), for easy use and very easy change.

As shown in 3 and 4, the cigarette bottle assembly includes a hollow cigarette holder shell (b), and a perforated component for liquid storage (9) inside the shell (b). The perforated component for liquid storage (9) is made of such materials as PLA fiber, terylene fiber or nylon fiber, which are suitable for liquid storage. Alternatively, it may be plastic foam molding or column of multi-layer plates made through plastic injection with polyvinyl chloride, polypropylene and polycarbonate. One end of the cigarette holder shell (b) plugs into the shell (a), and the outer peripheral surface of the cigarette holder shell (b) has an inward ventilating groove (b2). On one end surface of the cigarette holder shell (b), there is an air channel (b1) extending inward. The air channel (b1) is located in the center on the surface of one end of shell (b).

Figure 20:
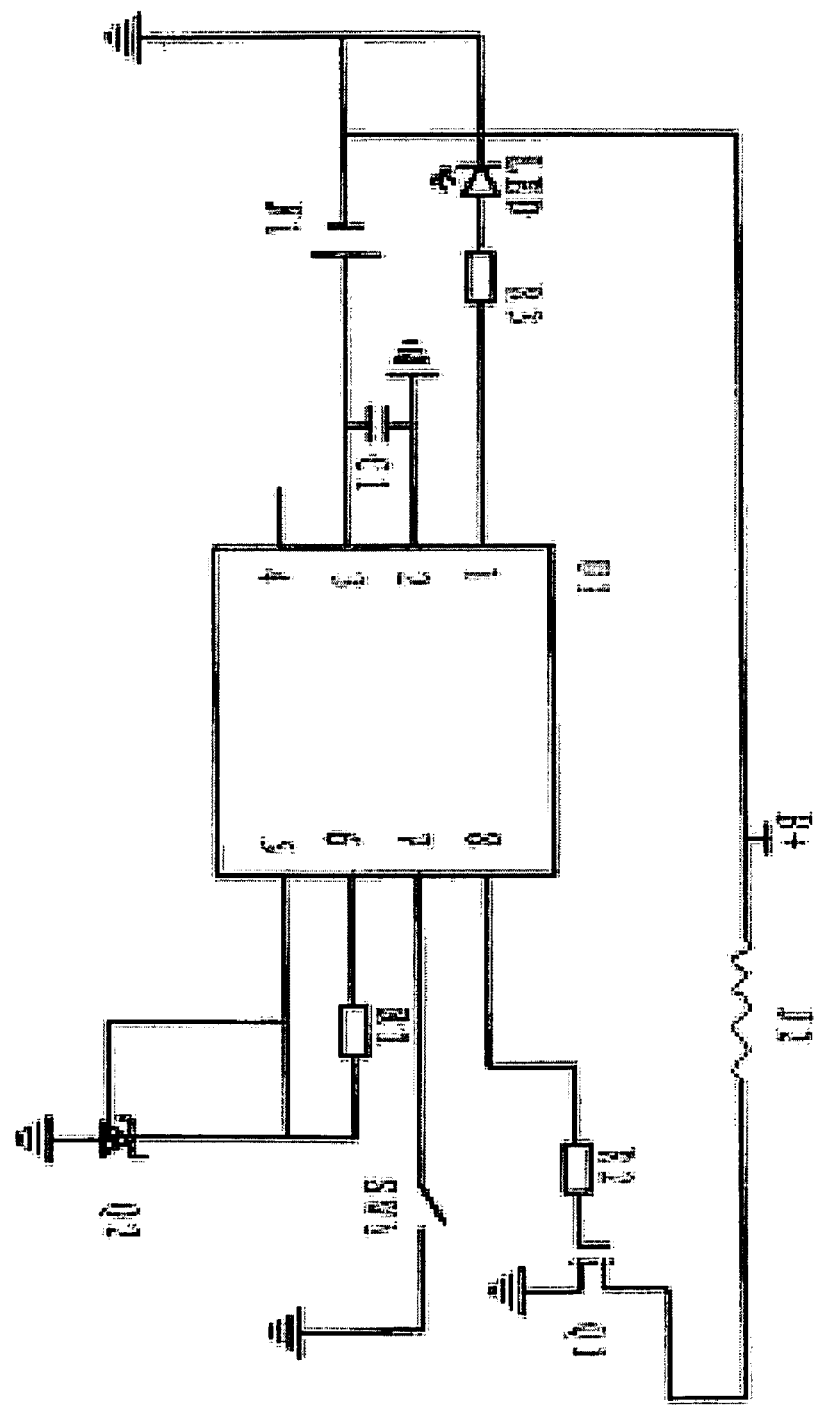
FIG. 20 is the electric circuit diagram of the electronic cigarette of this invention, with the airflow sensor adopting a reed relay structure.

As shown in FIG. 1-9, one end of the porous component (81) lies against one end surface of the said perforated component for liquid storage (9), and contacts the perforated component for liquid storage (9). It absorbs the cigarette liquid from the perforated component for liquid storage (9). When the smoker smokes, the cavity of the cigarette holder shell (b) is in the negative pressure state. In the shell (b), one end of the airflow sensor (5) forms a normal pressure cavity, while the other end forms a negative pressure cavity. The air pressure difference between the normal pressure cavity and negative pressure cavity or the high-speed airflow enables the magnetic steel (54) of the airflow sensor (5) to drive the reed relay(52) to contact the relay electrode (51). As shown in FIG. 20, the electric circuit is electrified, and the electronic switch circuit on the electronic circuit board (4) is electrified. Thus, the rechargeable battery (3) starts to electrify the electric heating rod (82) inside the atomizer (8), and at the same time, the LEDs, which are electrified by the rechargeable battery (3), emit light. The air enters the normal pressure cavity through the air inlet (a1), passes the check valve (7) via the airflow passage in the airflow sensor (5), and flows to the negative pressure cavity (83) in the atomizer (8). Since the negative pressure cavity (83) provides the negative pressure compared with the outside, the air flow sprays into it, bringing the cigarette liquid from the porous component (81) to spray into the negative pressure cavity (83) in the form of fine drips. In the meantime, the electric heating rod (82) is electrified by the rechargeable battery (3) under the control of electronic circuit board (4), to heat the fine drips for atomization. After atomization, the big-diameter fine drips are re-absorbed by the porous component (81) under the action of vortex, while the small-diameter fine drips are suspended in the airflow to form gasoloid, which is discharged through the negative pressure cavity (83) and run-through hole (813), flows into the cigarette holder shell (b) of the cigarette bottle assembly, and is absorbed by the air channel (b1). When the gasoloid enters the cigarette holder shell (b), multiple small liquid drips are condensed into bigger ones, which fall into the clearance between the cigarette holder shell (b) and air channel (b1) without being absorbed by the air channel (b1). The perforated component for liquid storage (9) of the cigarette bottle assembly and the porous component (81) of the atomizer (8) contact each other to achieve the capillary impregnation for liquid supply.

The unit and its connecting structure of this invention may also be loaded with drugs for delivery to the lung.

Figure 22:
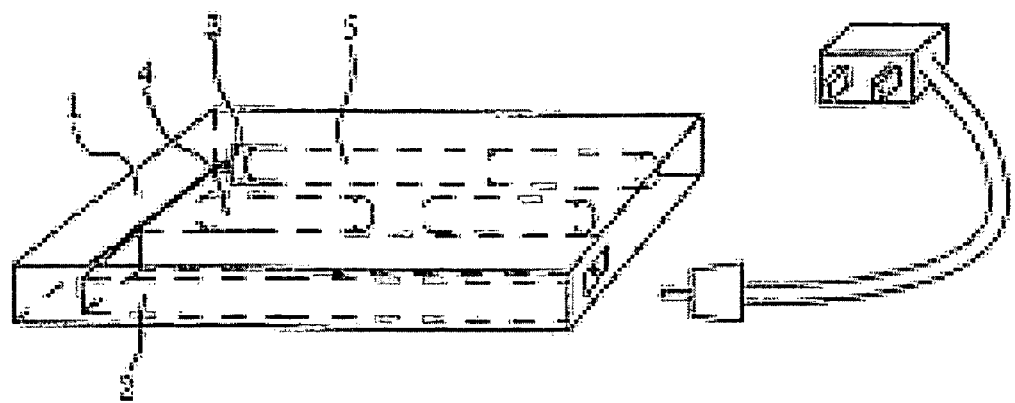
FIG. 22 is the diagram of the cubic structure of the charging device of this invention, illustrating the locations of and connection relation of various internal parts.
Figure 23:
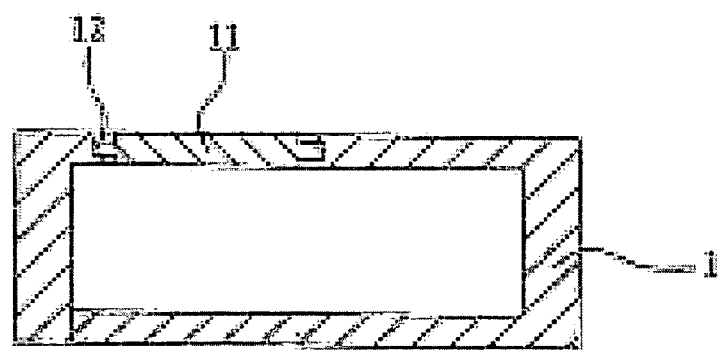
FIG. 23 is the side section view of the charging device of this invention, illustrating the structure of slide way and cover.
Figure 24:
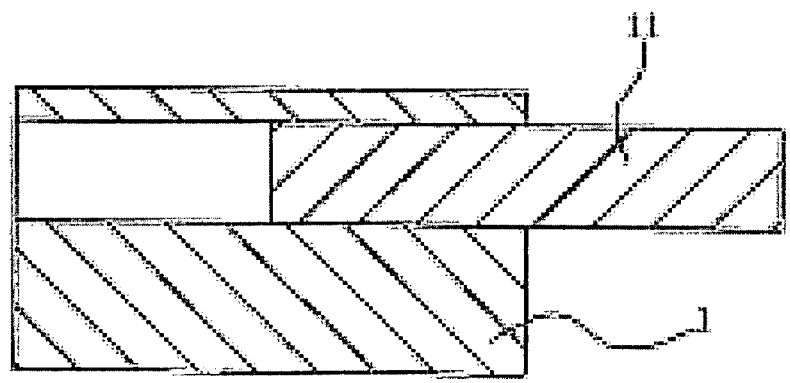
FIG. 24 is the diagram of the front structure of the charging device of this invention, illustrating the structure of the sliding cover.

As shown in FIGS. 22, 23 and 24, the electronic cigarette (5) is held in a charging device. The charging device includes a case (1), which contains an auxiliary charging storage battery (2) inside it, and holds the electronic cigarette (5) and the charger (3) for the rechargeable battery embedded in the electronic cigarette (5), as well as the power supply circuit. The power inputs of the auxiliary charging storage battery (2) and charger (3) are connected with the power supply respectively. The charger (3) in this embodiment is a constant voltage & current charger. It may be a GY5210 charger, or any other constant voltage & current charger. The case (1) has a spare liquid supply bottle (4) in it. The power output of the auxiliary charging storage battery (2) is connected with the power input of the charger (3). The power output of the charger (3) is a charging slot (31), which fits with the charging plug of the rechargeable battery inside the electronic cigarette, or a charging plug, which fits with the charging slot of the rechargeable battery.

As shown in FIGS. 23 and 24, on the body of the shell (1), there is a pair of slide ways (12) corresponding to the position of the electronic cigarette, and on the slide ways, there is a slide cover (11).

In the second preferred embodiment of this utility model, a restriction component (10), which is detachable, is set on one end of the said porous component (81). There is a restriction hole (101) on the body of the restriction component (10). The restriction hole (101) corresponds to the atomizing chamber (811). The pore diameter of the restriction hole is less than the inner diameter of the atomizing chamber (811) to the extent that the size of the restriction component (10) installed on the porous component (81) varies, for the purpose of airflow capacity control. On the basis of different applications, the restriction component of different sizes and pore diameters may be used.

In the third preferred embodiment of this utility model, as shown in 11 and 12, on the outer peripheral wall of the cigarette shell (b), there is a protruding rib (b2) that is evenly partitioned. The perforated component for liquid storage (9) enters the cigarette holder shell (b) and lies against the protruding rib (b2). Thus, there appears a clearance between the outer peripheral surface of the perforated component for liquid storage (9) and the interior wall of the shell (b). The clearance is for connection the shell (a) and cigarette holder shell (b). When the user smokes, the air channel (b1) absorbs the air to cause airflow inside the shell (a), thus triggering the airflow sensor (5) and eventually starting the electronic cigarette. Also, the atomizer (8) works to atomize the cigarette liquid and produce gas flow, which enters the cigarette holder shell (b).

In the fourth preferred embodiment of this utility model, as shown in FIGS. 13, 14, 15 and 16, on one end of the cylinder (821), there is a fixed plate (84), whose outer peripheral wall has partitioned supports (841). The outer ends of the supports (841) lie against the interior wall of the shell (a), thus suspending the cylinder (821), which is connected with the fixed plate (84), in the cavity of the shell (a). On the surface of the fixed plate (84), there is a mandril (842), whose front end lies against one end of the porous component (81), so that the fixed plate (84) is separated from the atomizing chamber (811) of the porous component (81). As a result, the run-through hole on one end of the atomizing chamber (811) won't be blocked, and the mist generated in the atomizing chamber (811) can be dispersed. One end of the porous component (81) has two protuberances (812) at the outlet of the atomizing chamber (811). Between the two protuberances (812) is a clearance. The two protuberances (812) lie against the perforated component for liquid storage (9).

Figure 17:
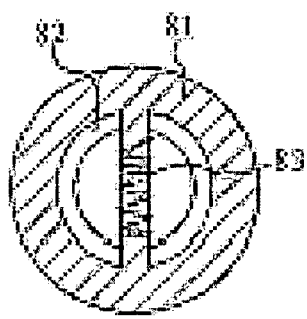
FIG. 17 is the diagram of the axial structure of the atomizer in the fifth preferred embodiment of this invention.
Figure 18:
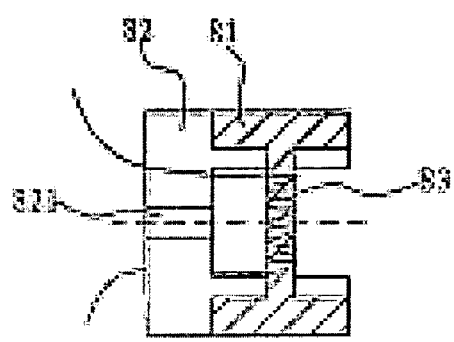
FIG. 18 is the side section view of the atomizer in the fifth preferred embodiment of this invention.

In the fifth preferred embodiment of this utility model, as shown in FIGS. 17 and 18, the atomizer assembly is an atomizer (8), which includes a frame (82), the porous component (81) set on the frame (82), and the heating wire (83) wound on the porous component (81). The frame (82) has a run-through hole (821) on it. The porous component (81) is wound with heating wire (83) in the part that is on the side in the axial direction of the run-through hole (821). One end of the porous component (81) fits with the cigarette bottle assembly. The porous component (81) is made of foamed nickel, stainless steel fiber felt, macromolecular polymer foam or foamed ceramics.

Figure 19:
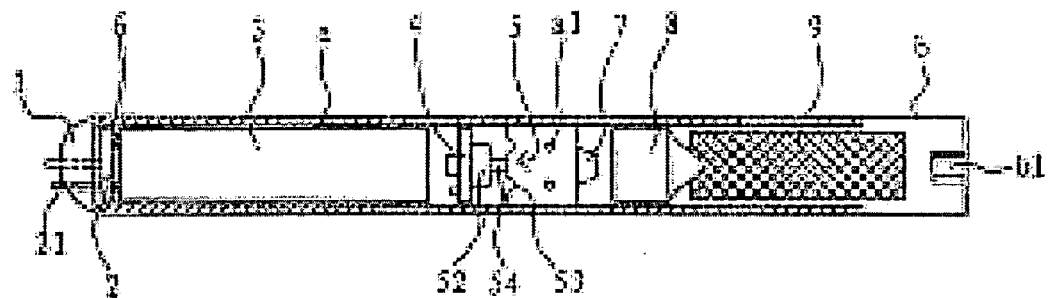
FIG. 19 is the side section view of the electronic cigarette in the sixth preferred embodiment of this invention, illustrating the diagram of the structure of the airflow sensor adopting Hall element.
Figure 21:
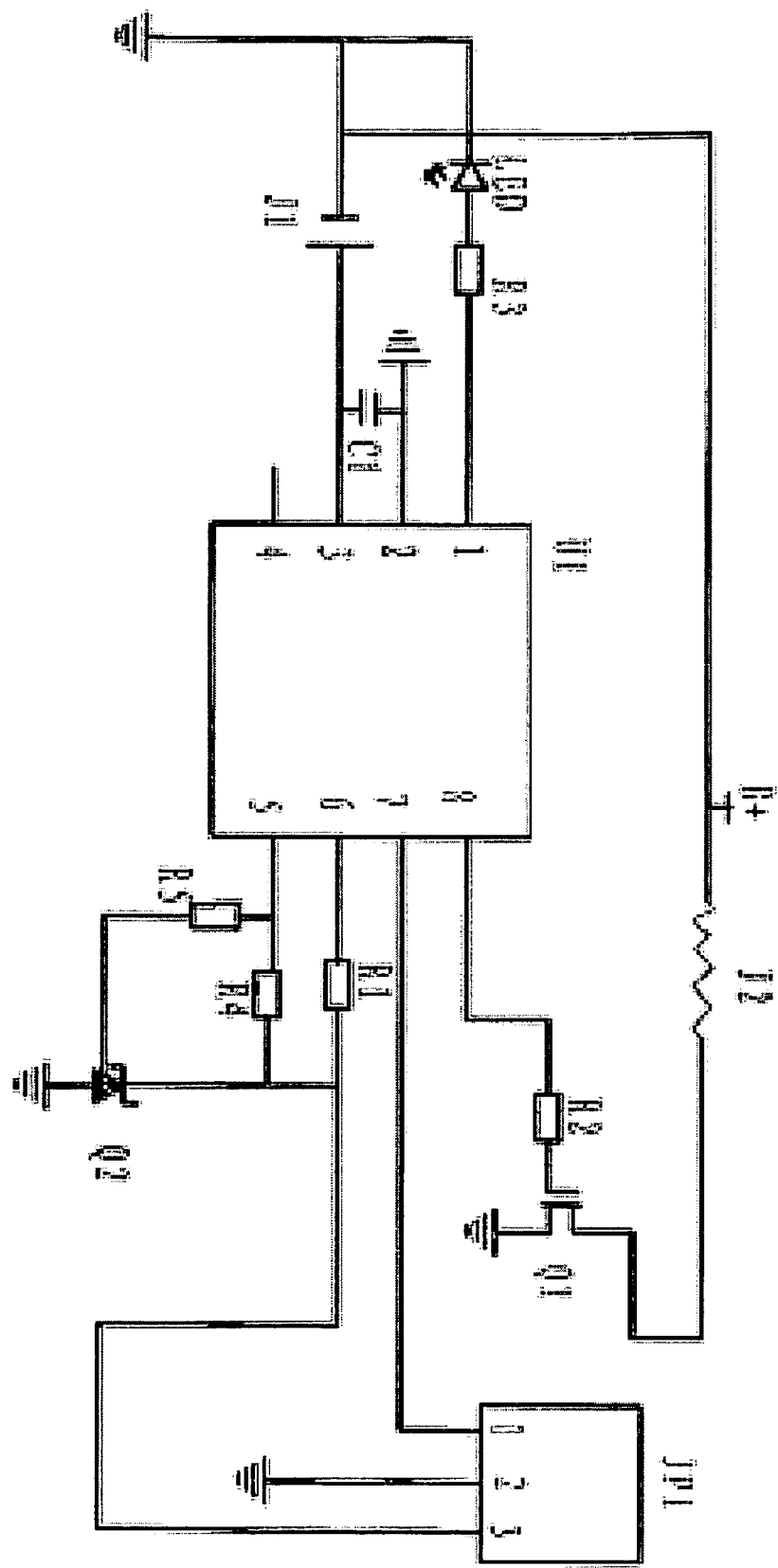
FIG. 21 is the electric circuit diagram of the electronic cigarette of this invention, with the airflow sensor adopting Hall element.

In the sixth preferred embodiment of this utility model, as shown in FIG. 19, the airflow sensor (5) has a silica gel corrugated membrane (53), which connects with magnetic steel (54) with a Hall element (52), or a magneto-diode or a magneto-triode on one of its ends. FIG. 21 shows the electric circuit of the electronic cigarette of this solution.

The invention claimed is:

1. An aerosol electronic cigarette, comprising:
a battery assembly, an atomizer assembly, a cigarette-solution storage area, and a hollow shell having a mouthpiece: the battery assembly connects with the atomizer assembly, and both are located in the shell; the cigarette solution storage area is located in one end of the shell adjacent to the mouthpiece, and fits with at least a portion of the said atomizer assembly inside it; the shell has through-air-inlets; the atomizer assembly includes an atomizer comprising an electric heating rod and a run-through atomizing chamber; the electric heating rod comprises a cylinder and a heating element provided at the wall of the cylinder, the electric heating rod is in the said atomizing chamber and there is a negative pressure cavity in the atomizing chamber.

2. An aerosol electronic cigarette according to claim 1, further comprising a cigarette solution in the cigarette solution storage area, the cigarette solution comprising nicotine.

3. An aerosol electronic cigarette according to claim 1, wherein the shell comprises first and second detachable sections.

4. An aerosol electronic cigarette of claim 3, wherein the first detachable section comprises the mouthpiece.

5. An aerosol electronic cigarette according to claim 1, wherein the heating element is a coiled wire.

6. An aerosol electronic cigarette according to claim 5, wherein the coiled wire extends along the length of the cylinder.

7. An aerosol electronic cigarette according to claim 5, wherein the coiled wire is on the outer surface of the cylinder.

8. An aerosol electronic cigarette according to claim 1, wherein the cylinder is inside the run through chamber.

9. An aerosol electronic cigarette of claim 1, wherein the solution storage area comprises a cigarette-bottle assembly.

10. An aerosol electronic cigarette, comprising:
a battery assembly, an atomizer assembly, a cigarette solution storage area, and a shell that is hollow and comprises a mouthpiece: the said battery assembly connects with the said atomizer assembly, and both are located in the said shell; the said cigarette solution storage area is located in one end of the shell proximal to the mouthpiece, and fits with at least a portion of the said atomizer assembly inside it; the said shell has through-air-inlets; the atomizer assembly is an atomizer, which includes a porous component and an electric heating rod; wherein the electric heating rod comprises a cylinder and a heating element provided at the wall of the cylinder, the said porous component has a run-through atomizing chamber; the electric heating rod is in the said atomizing chamber and there is a negative pressure cavity in the atomizing chamber.

11. An aerosol electronic cigarette of claim 10, wherein a restriction component is detachably set on one end of the said porous component; there is a restriction hole on the principal part of the said restriction component; the said restriction hole corresponds to the said atomizing chamber; the diameter of the said restriction hole is less than the inner diameter of the atomizing chamber.

12. An aerosol electronic cigarette of claim 10, wherein the said battery assembly includes a battery, and an operating indicator, an electronic circuit board, and an airflow sensor, which are connected with the said battery; the signal output of the said airflow sensor is connected with the said electronic circuit board.

13. An aerosol electronic cigarette of claim 12, wherein the said shell comprises a check valve; the said battery is a rechargeable battery, which has a flexibly connected charging plug; wherein blades of the said charging plug come out of the other end of the said shell.

14. An aerosol electronic cigarette of claim 13, wherein between the said charging plug and rechargeable battery is a spring, which lies against the principal part of the said rechargeable battery on one end, and against the said charging plug on the other free end.

15. An aerosol electronic cigarette of claim 12, wherein the said battery is a rechargeable battery, which has a charging slot on it;
the said operating indicator comprises a LED.

16. An aerosol electronic cigarette of claim 12, wherein the said airflow sensor comprises a semiconductor force-sensitive chip capacitance sensor or an inductance sensor.

17. An aerosol electronic cigarette of claim 12, wherein the said electronic circuit board includes an electronic switch circuit.

18. An aerosol electronic cigarette of claim 12, wherein the said airflow sensor has a silica gel corrugated membrane, which connects with magnetic steel with a reed relay on one of its ends; both ends of the said reed relay correspond to relay electrodes respectively.

19. An aerosol electronic cigarette of claim 12, wherein the said airflow sensor has a silica gel corrugated membrane, which connects with magnetic steel with a Hall element or a magneto-diode or a magneto-triode on one of its ends.

20. An aerosol electronic cigarette of claim 10, wherein the said porous component is made of foamed nickel, stainless steel fiber felt, polymer or ceramics.

21. An aerosol electronic cigarette of claim 10, wherein the said cigarette solution storage area includes a hollow mouthpiece-shell, and a perforated component for liquid storage inside the shell; one end of the said mouthpiece shell plugs into the said shell.

22. An aerosol electronic cigarette of claim 21, wherein the said air channel is located in the center of one end surface of the said cigarette holder shell.

23. An aerosol electronic cigarette of claim 21, wherein one end of the said porous component lies against one end surface of the said perforated component for liquid storage, and contacts the perforated component for liquid storage.

24. An aerosol electronic cigarette of claim 21, wherein the said perforated component for liquid storage comprises PLA fiber, terylene fiber or nylon fiber.

25. An aerosol electronic cigarette of claim 21, wherein the said perforated component for liquid storage comprises plastic foam molding, or column of multi-layer plates made through plastic injection with PVC, PP or PC.

26. An aerosol electronic cigarette of claim 10, wherein the said aerosol electronic cigarette is configured to connect to a charging device; the said battery is a rechargeable battery.

27. An aerosol electronic cigarette of claim 26, wherein the said charging device includes a case, which contains an auxiliary charging storage battery inside it, and holds the electronic cigarette and the charger for the rechargeable battery embedded in the electronic cigarette.

28. An aerosol electronic cigarette of claim 27, wherein the said case has a spare liquid supply bottle in it.

29. An aerosol electronic cigarette of claim 27, wherein the said power output of the auxiliary charging storage battery is connected with the power input of the charger.

30. An aerosol electronic cigarette of claim 27, wherein the power output of the said charger is a charging slot, which fits with a charging plug of the rechargeable battery inside the electronic cigarette, or a charging plug, which fits with the charging slot of the rechargeable battery.

31. An aerosol electronic cigarette of claim 30, wherein the said charger is a constant voltage and current charger.

32. An aerosol electronic cigarette of claim 27, wherein on the principal part of the said case, there is a pair of slide ways corresponding to the position of the said electronic cigarette, and on the slide ways, there is a slide cover.

33. An aerosol electronic cigarette of claim 10, wherein the heating element comprises a heating wire.

34. An aerosol electronic cigarette of claim 33, wherein the said heating wire is made of platinum wire, nickel-chromium alloy wire or iron-chromium alloy wire containing rare earth, or is flaked.

35. An aerosol electronic cigarette of claim 10, wherein the heating element comprises a coiled heating wire, which is wound at the wall of the cylinder.

36. An aerosol electronic cigarette of claim 10, wherein the solution storage area comprises a cigarette-bottle assembly.

37. An aerosol electronic cigarette of claim 10, wherein the electric heating element is provided outside the wall of the cylinder.

38. An aerosol electronic cigarette of claim 10, further comprising a cigarette solution comprising nicotine.

39. An aerosol electronic cigarette, comprising:
a battery assembly, an atomizer assembly, a cigarette-solution storage area, and a shell that is hollow: the said battery assembly connects with the said atomizer assembly, and both are located in the said shell; the said cigarette solution storage area is located in one end of the shell, and fits with at least a portion of the said atomizer assembly inside it; the said shell has through-air-inlets; the atomizer assembly is an atomizer, which includes a porous component and an electric heating rod; wherein the electric heating rod comprises a cylinder and a heating element provided at the wall of the cylinder, the said porous component has a run-through atomizing chamber; the electric heating rod is in the said atomizing chamber and there is a negative pressure cavity in the atomizing chamber,
wherein said heating element is heating wire, which is wound on the wall of the cylinder; on the wall of both ends of the cylinder, there are mandrils respectively; the said porous component has a protuberance on one end, and the protuberance fits with the cigarette solution storage area; the said protuberance is a protruding half sphere, on the side of which there is a run-through hole connecting to the atomizing chamber.

40. An aerosol electronic cigarette of claim 39, wherein the said heating wire is made of platinum wire, nickel-chromium alloy wire or iron-chromium alloy wire containing rare earth, or is flaked.

41. An aerosol electronic cigarette, comprising:
a battery assembly, an atomizer assembly, a cigarette-solution storage area, and a shell that is hollow: the said battery assembly connects with the said atomizer assembly, and both are located in the said shell; the said cigarette solution storage area is located in one end of the shell, and fits with at least a portion of the said atomizer assembly inside it; the said shell has through-air-inlets; the atomizer assembly is an atomizer, which includes a porous component and an electric heating rod; wherein the electric heating rod comprises a cylinder and a heating element provided at the wall of the cylinder, the said porous component has a run-through atomizing chamber; the electric heating rod is in the said atomizing chamber and there is a negative pressure cavity in the atomizing chamber,
wherein said heating element is made of electrically conductive ceramic PTC material; the said heating element is set on the wall of the said cylinder; on the wall of both ends of the said cylinder, there are mandrils respectively; the said porous component has a protuberance on one end, and the said protuberance fits with the said cigarette solution storage area; the said protuberance is a half sphere, on the side of which there is a run-through hole connecting to the said atomizing chamber.

* * * * *